US012636305B2

(12) United States Patent  
Zaharako et al.

(10) Patent No.: US 12,636,305 B2  
(45) Date of Patent: May 26, 2026

(54) COMPOSITION AND METHOD OF APPLYING SAME TO INCREASE SURVIVAL OF FISH FOLLOWING CATCH-AND-RELEASE SITUATIONS

(71) Applicant: Dutch Creek Nymphing, LLC, Denver, CO (US)

(72) Inventors: James Seth Zaharako, Denver, CO (US); Slavko Komarnytsky, Concord, NC (US)

(73) Assignee: Dutch Creek Nymphing, LLC, Denver, CO (US)

( * ) Notice: Subject to any disclaimer, the term of this patent is extended or adjusted under 35 U.S.C. 154(b) by 524 days.

(21) Appl. No.: 18/125,335

(22) Filed: Mar. 23, 2023

(65) Prior Publication Data

US 2023/0321136 A1    Oct. 12, 2023

Related U.S. Application Data

(60) Provisional application No. 63/324,315, filed on Mar. 28, 2022, provisional application No. 63/323,231, filed on Mar. 24, 2022.

(51) Int. Cl.  
     *A61K 31/715*      (2006.01)  
     *A61K 45/06*      (2006.01)  
     *A61P 43/00*      (2006.01)

(52) U.S. Cl.  
     CPC ............ *A61K 31/715* (2013.01); *A61K 45/06* (2013.01); *A61P 43/00* (2018.01)

(58) Field of Classification Search  
     None  
     See application file for complete search history.

(56) References Cited

U.S. PATENT DOCUMENTS

| | | |
|---|---|---|
| 4,500,510 A | 2/1985 | Goldstein |
| 5,882,647 A | 3/1999 | Yoshpa |
| 5,942,232 A | 8/1999 | Costa |
| 6,269,586 B1 | 8/2001 | Jones |
| 6,518,252 B2 | 2/2003 | Wooley et al. |
| 7,347,944 B2 | 3/2008 | Bagley |
| 7,434,529 B2 | 10/2008 | Tipton |
| 8,393,110 B2 | 3/2013 | Ball |
| 8,806,800 B2 | 8/2014 | HJupp et al. |
| 9,572,329 B2 | 2/2017 | Hopkins |
| 10,933,388 B1 | 3/2021 | Falcone |
| 11,229,196 B1 | 1/2022 | Sohnle |
| 11,234,425 B2 | 2/2022 | Pearce |
| 2002/0098208 A1 | 7/2002 | Wooley et al. |
| 2006/0219184 A1 | 10/2006 | Wilson et al. |
| 2009/0099251 A1 | 4/2009 | De Saizieu et al. |
| 2009/0270513 A1 | 10/2009 | Goralczyk et al. |
| 2009/0288611 A1 | 11/2009 | Gergely et al. |
| 2010/0048688 A1 | 2/2010 | Fowler et al. |
| 2010/0074976 A1 | 3/2010 | Fowler et al. |
| 2010/0281752 A1 | 11/2010 | Daley, Jr. et al. |
| 2010/0317727 A1 | 12/2010 | De Saizieu et al. |
| 2010/0317728 A1 | 12/2010 | Fowler et al. |
| 2011/0225660 A1 | 9/2011 | Streitenberger et al. |
| 2011/0300228 A1 | 12/2011 | Breivik et al. |
| 2012/0171310 A1 | 7/2012 | Brodie et al. |
| 2012/0244234 A1 | 9/2012 | Etheve et al. |
| 2013/0156816 A1 | 6/2013 | Stobbs et al. |
| 2014/0044812 A1 | 2/2014 | Al-Yaqout et al. |
| 2014/0375298 A1 | 12/2014 | Garcia et al. |
| 2021/0251257 A1 | 8/2021 | Srinivasan |

OTHER PUBLICATIONS

Pena-Verdeal H, Garcia-Queiruga J, García-Resúa C, Yebra-Pimentel E, Giráldez MJ. Osmolality and pH of commercially available contact lens care solutions and eye drops. Contact Lens and Anterior Eye. Aug. 1, 2021;44(4):101379.*

Mariggio et al. Int. J. Immunopathol. Pharmacol. (2009), vol. 22, No. 2, pp. 485-492.*

R.A. Ferguson and B.L. Tufts; Physiological Effects of Brief Air Exposure in Exhaustively Exercised Rainbow Trout (*Oncorhynchus mykiss*): Implications for "Catch and Release" Fisheries; Canadian Journal of Fisheries and Aquatic Sciences—Jun. 1992; 7 pgs.

S.J. Cooke & G.D. Raby; The Physiological Consequences of Catch-and-Release-Angling: Perspectives on Experimental Design, Interpretation, Extrapolation and Relevance to Stakeholders; Fisheries Management and Ecology, 2013, 20, 268-287; 20 pgs.

Aaron Bartholomew and James A. Bohnsack; A Review of Catch-and-Release Angling Mortality With Implications for No-Take Reserves; Reviews in Fish Biology and Fisheries (2005) 15: 129-154; 26 pgs.

(Continued)

*Primary Examiner* — Patrick T Lewis

(74) *Attorney, Agent, or Firm* — Vedder Price P.C.

(57) ABSTRACT

The invention relates to a composition and method to increase survival of fish following catch-and-release events. The composition comprises an energy substrate and a hydrocolloid. The composition may comprise an application-safe buffer. The energy substrate may be a glycolysis metabolite, a Krebs cycle metabolite, an amino acid, a nitric oxide donor, a triglyceride, and mixtures thereof. The hydrocolloid may be a polysaccharide. The composition may include an oxygenated substrate, a trophic hormone, a stress reducing additive, a chelating agent, an antimicrobial preservative, and a color additive, and mixtures thereof. The method comprises after catching the fish, applying the composition to the fish and releasing the fish back into the wild. The composition may alternatively be mixed with a flotant or a cured polymer in the shape of a lure such that composition may be dispersed onto the oxygen exchange tissue of the fish when it is caught.

11 Claims, No Drawings

(56)          References Cited

OTHER PUBLICATIONS

Takuji Usui et al.; The French Press: a Repeatable and High-Throughput Approach to Exercising Zebrafish (*Danio rerio*); (2018), PeerJ, DOI 10.7717/peerj.4292; 12 pgs.

* cited by examiner

COMPOSITION AND METHOD OF APPLYING SAME TO INCREASE SURVIVAL OF FISH FOLLOWING CATCH-AND-RELEASE SITUATIONS

CROSS REFERENCE TO RELATED APPLICATIONS

This application claims the benefit of and priority to U.S. Provisional Application No. 63/323,231, filed Mar. 24, 2022 and U.S. Provisional Application No. 63/324,315, filed Mar. 28, 2022, the content of which is hereby incorporated by reference.

BACKGROUND

Sport fishing is a popular pastime throughout the United States and the world. Catch-and-release fishing is an increasingly popular practice within sport fishing that involves releasing a caught fish back into the water. Catch-and-release fishing has increased in popularly in recent decades, reflecting anglers' desires to support conservation, animal well-being, sustainability, and stewardship. Anglers utilize this practice with the goal that the released fish may continue to live, breed, and potentially be caught on a separate occasion.

Post-Release Mortality Factors

Despite this laudable goal, the fish is nonetheless exposed to numerous stressors that lower the fish's chance of survival following release. A substantial number dies after release. One meta-analysis of 53 release studies estimates that the average mortality rate for released fish was 18%. (See Bartholomew, A., Bohnsack, J. A. A Review of Catch-and-Release Angling Mortality with Implications for No-take Reserves. Rev Fish Biol Fisheries 15, 129-154 (2005)).

The practice of catch-and-release sport fishing involves catching, playing, landing, dehooking, photographing, measuring, and releasing the fish. Nearly all these steps involve additional stressors on the fish which lower its chances of survival after it is released.

Stressors to the fish begin when the fish is hooked. Most hooks are barbed and puncture a hole in the fish's mouth. When hooks are barbed, it can be difficult to remove the hook without handling the fish for an increased amount of time, or without causing additional harm to the fish. The puncture left after a hook is removed may become infected. The longer times spent to fight, land, record, and release the hooked fish increase adverse effects to the fish and directly harm fish health and wellbeing. These additional stressors further contribute to post-release mortality. (See S. Cooke, M. Donaldson, C. O'Connor, G. Raby, R. Arlinghaus, A. Danylchuk, K. Hanson, S. Hinch, T. Clark, D. Patterson The physiological consequences of catch-and-release angling: perspectives on experimental design, interpretation, extrapolation and relevance to stakeholders Fish. Manag. Ecol., 20 (2013), pp. 268-287).

Exhaustion is another fish stressor and mortality factor. During its fight with an angler, a fish will expend considerable amounts of energy resisting. When released back into the water, the fish will be exhausted having used up a considerable amount of its available energy. Water temperatures at either extreme, cold or warm, intensify the stressors to the fish being caught in these environments making it more difficult for the fish to recover. Similarly, heavily pressured waters where fish may be caught multiple times in short periods of time, exacerbate fish exhaustion and inhibit the ability of fish to recover on its own after release. This decreases a fish's fitness and increases its vulnerability to predation.

Yet another cause of increased fish mortality following release results from oxygen deprivation. Nearly all fish are unable to respire out of water. Fish gills have adapted to exchange gases in oxygenated water and are ill-adapted to respire in the open air. When a fish is removed from the water, to remove a hook from its mouth, not to mention being weighed, measured, and/or photographed, the fish is deprived of oxygen. Even limited exposure to the air can decrease survival rates for released fish. For example, one study determined that fish that were hooked, landed, and released without being exposed to the air resulted in a survival rate of 88%. Fish that were removed from the water for 30 seconds had a post-release survival rate of 62%. And fish that were removed from the water for 60 seconds resulted in a post-release survival rate of only 28%. (Ferguson and Tufts, 1992). Tired and exhausted fish need to increase oxygen intake and balance their metabolism rapidly to have best chances of recovery.

Past Solutions

In recognition of the harm done to fish caught by anglers and the increasing desire among anglers to successfully release fish back into the wild, there have been some solutions proposed. Most of them have been behavioral recommendations, such as recommendations from fish and wildlife management authorities and/or researchers who advocate for limited exposure to the air for the fish.

There have also been some limited technical innovations that sought to improve fish health. For example, U.S. Pat. No. 9,572,379 discloses an anti-microbial fish hook. More specifically, the '379 patent discloses a hook that is plated or coated with a substance to treat injury to fish caused by impalement by the hook. The disclosed hook may be plated with a metal known to have anti-microbial properties, such as copper or silver, or coated in an antimicrobial substance such as sodium percarbonate. The '379 patent also teaches that the coated substance may also be formulated to reduce stress or inflammation caused during impalement. However, there are notable limitations to the teachings of the '379 patent. Most significantly, the antimicrobial coating is water soluble, and therefore, any potential benefit that may have been contemplated for a hooked fish are diluted if not completely washed away upon submersion into the body of water from which the fish is subsequently hooked. Further, any benefits from the hook taught by the '379 patent are directed at reducing harm cause by the hook and not to the struggle the fish exerts during landing or the harm caused by oxygen deprivation when handled out of the water.

Another technical innovation that sought to improve the wellbeing of fish is disclosed in U.S. Patent Application No. 2006/0219184. In the '184 application, the invention was a plastic bag designed to release chemicals to the fish placed within during transportation. This disclosure was designed specifically to reduce stress for fish in the aquaculture industry by releasing pH balancing chemicals, stress-reducing chemicals, oxygen-generating chemicals, carbon dioxide regulating chemicals, ammonia regulating chemicals, salt regulating chemicals, tranquilizing chemicals, water purifying chemicals, disease controlling chemicals, and mixtures thereof. The disclosure of the '184 application's is inapplicable in a catch-and-release situation for at least two major reasons: first, the catch-and-release fish is generally not maintained in a pool of water, especially during playing, landing, dehooking, photographing, and measuring and second, by definition, the fish is being released back into open waters where the solution of the '184 application would be too diluted to be significantly beneficial. Another fundamental distinction is found in the difference between stressors on fish in an aquaculture environment from the stressors a fish caught from a river, stream, lake, or ocean, most notably, the oxygen deprivation that accompanies handling after being caught. Further, the goal of maintaining the fish in the aquaculture environment of the '184 application can be consumption, not release back into the fish's natural habitat. Thus, the '184 application fails to provide the necessary teachings to improve post-release mortality for fish that have been caught and subsequently released back into the wild by anglers. When the goal is not consumption, such as during a tournament where a fish is held in a plastic bag to be measured prior to release, the '184 application further contributes to the stressors of a caught fish by confining the fish out of its habitat. Finally, the plastic bags disclosed by the '184 application would be inapplicable for many sport fish, which are large, and which would make it impracticable to use the '184 disclosure.

SUMMARY OF THE DISCLOSURE

The present invention is directed at a composition and method for increasing the survival of fish in a catch-and-release situation. The disclosed intervention delivers oxygen to oxygenate gills and other tissues, supplies energy through Krebs cycle when oxygen is present, promotes mitochondrial ATP production and improves mitochondria substrate utilization, stimulation, and release of native mucus production, lowers cortisol, provides a localized anesthetic, or strengthens immune response.

More particularly, the present invention is a composition, comprising an energy substrate, a pH buffer, and a hydrocolloid. The composition may further comprise an oxygenated substrate, a trophic hormone, a stress-relieving additive, a chelating agent, and an antimicrobial preservative. The composition may be administered to a fish orally, to the fish's gills, topically, internally, or anally. The disclosed composition can be applied to any oxygen-exchanging organs on the fish, including, the skin, gills, labyrinth, esophagus, stomach, intestine, or swim bladder. Administration of the composition may be accomplished via a pill, an ingestible coating, an injection, a microcapsule, a wash, a dropper, an emersion, a spray, a solution, a cream, a paste, a gel, or as part of ingestible or artificial bait, as part of a lure, or as part of a floatant.

DETAILED DESCRIPTION

The present invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods or devices. The following detailed description is, therefore, not to be taken in a limiting sense.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "and combinations thereof" as used herein refers to all permutations or combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The use of the terms "at least one" and "one or more" will be understood to include one as well as any quantity more than one, including, but not limited to, each of, 2, 3, 4, 5, 10, 15, 20, 30, 40, 50, 100, and all integers and fractions, if applicable, therebetween. The terms "at least one" and "one or more" may extend up to 100 or 1000 or more, depending on the term to which it is attached; in addition, the quantities of 100/1000 are not to be considered limiting, as higher limits may also produce satisfactory results.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

In an effort to substantially reduce fish mortality following catch-and-release practices, a composition is disclosed for application to the fish primarily while the fish is out of water, however, it will be possible to administer the composition in some circumstances when a fish is partially or wholly submerged in the water, such as administrations accomplished orally or anally using a gavage type technique, a pill or paste, or via a lure designed to deliver the composition to the fish when it is hooked. While it is best practice to keep a caught fish partially under water so that any administration of the disclosed composition will only minimally remove a portion of the fish from the water, some anglers may continue to remove the entire fish out of the water for photographing and weighing. This continuing practice underscores the need for the disclosed composition to improve the mortality rate of fish following a catch-and-release situation. The composition preferably includes an energy substrate, a buffer, and a hydrocolloid. Various embodiments of the composition may also include one or more of the following: an oxygenated substrate, a trophic hormone, a stress-relieving additive, a chelating agent, or an antimicrobial substance.

Energy Substrate. The composition preferably contains an energy substrate to substantially aid the fish by replenishing some of the energy expended by the fish in resisting being caught by the angler. The energy substrate could be pyruvate, which supplies energy through glycolysis. The energy substrate could be succinate, which supplies energy through the Krebs cycle when oxygen is present. The energy substrate could also be leucine, which promotes mitochondrial ATP production. The energy substrate could also be arginine, which increases nitrogen oxide production and can widen blood vessels. The energy substrate could also be glycerol which facilitates glycogen restoration in the presence of lactate and which also has antimicrobial properties. The energy substrate could be oxygen dissolved under pressure in the composition, or an oxygenated substrate. The inventors presently anticipate that oxygen or an oxygenated substrate will be preferred. In addition to leucine, the energy substrate could be comprised of other amino acids, such as arginine.

pH Buffer. The composition preferably includes a pH buffer. The pH buffer is used to substantially maintain the composition within a pH range that will protect the fish's epidermis, eyes, gills, and other physical attributes from experiencing a chemical burn as a result of the application of the composition to the fish. Preferably, the buffer will maintain the pH of the composition to between approximately 7.0 and 9.0. The buffer may comprise, for example and without limitation, a phosphate buffered saline solution or tris(hydroxymethyl)aminomethane buffer.

Although the preferred pH buffer range is 7.0-9.0, in subsequent testing, applicant determined that other pH ranges were acceptable. Generally, a pH between approximately 6.5 to 8.0 is considered optimal for most freshwater species of fish. Natural, unpolluted rainwater has a pH of approximately 5.6-5.8, and a lake will have a pH approximately between 6.0 and 9.0. The ocean has a pH of approximately 8.14 (and is becoming more acidic). It is generally known that a water environment with a pH below 5.5 can be fatal to certain species of fish (notably rainbow trout, which are particularly sensitive to pH levels), and a pH below 4.2 is generally considered fatal to most species of fish. However, taking the data in context, low pH environments have been shown to be harmful to fish when the fish experience prolonged exposure to such environments. Surprisingly, Applicant found that temporary exposure to the novel composition having a relatively low pH did not appear to have a significant adverse impact on the fish's health. This is likely due to the short period of exposure given the relatively quick reintroduction of the fish into the water. In view of the foregoing observation, several alternative approximate pH ranges are disclosed for various embodiments of the com-

6 position: 4.5-9.0; 4.5-8.5; 4.5-8.0; 4.5-7.5; 4.5-7.0; 4.5-6.5; 4.5-6.0; 4.5-5.5; 4.5-5.0; 5.0-9.0; 5.0-8.5; 5.0-8.0; 5.0-7.5; 5.0-7.0; 5.0-6.5; 5.0-6.0; 5.0-5.5; 5.5-9.0; 5.5-8.5; 5.5-8.0; 5.5-7.5; 5.5-7.0; 5.5-6.5; 5.5-6.0; 6.0-9.0; 6.0-8.5; 6.0-8.0; 6.0-7.5; 6.0-7.0; 6.0-7.0; 6.0-6.5; 6.5-9.0; 6.5-8.5; 6.5-8.0; 6.5-7.5; 6.5-7.0; 7.0-8.5; 7.0-8.0; 7.0-7.5; 7.5-9.0; 7.5-8.5; 7.5-8.0; 8.0-9.0; 8.0-8.5; and 8.5-9.0.

Hydrocolloid. The composition also preferably includes a hydrocolloid, which is a breathable gel that would at least temporarily adhere to the epidermis, eyes, gills, or any other location on a fish having tissue associated with oxygen exchange to which the composition is applied. In this manner, the hydrocolloid retains the overall composition on the fish for a certain period of time. That certain period of time may be manipulated by selecting the appropriate gel. For instance, the gel may be formed by carboxymethylcellulose (CMC), which is an anionic, water-soluble cellulose derivative. The solubility of CMC depends on its degree of polymerization as well as the degree of substitution and the uniformity of the substitution distribution. These variables may be manipulated to delay dissolution of the gel and thus prolong contact between the constituents of the composition and the fish to which it was administered. The hydrocolloid could also be, for example, chia seeds with a hydrated outer layer or a non-starch polysaccharide. The hydrocolloid may also comprise a polyvinylpyrolidene (PVP), polyethylene glycol (PEG), hyaluronic acid, gelatin, or agar. The hydrocolloid may also serve an additional function of being a binder that keeps the composition and its components together.

It is also believed that the application of the hydrocolloid to the exterior of the fish may allow the fish to retain more of its protective mucus even if it is physically contacted by an ungloved or otherwise dry hand of the angler.

Supplemental Components. Additional supplements may also be included in the composition. These supplemental components may include an oxygenated substrate, a trophic hormone, a stress relieving additive, a chelating agent, an antimicrobial substance, or a preservative. Each of these supplemental components may each individually increase the likelihood of survival for a fish following release. For instance, the oxygenated substrate would aid the fish in respiration and limit the total oxygen deprivation the fish experiences out of the water. A trophic hormone would aid the fish by encouraging natural mucus production while the fish is out of water. A stress relieving additive would aid the fish by providing stress reducing compounds. Chelating agents would aid the fish by reducing levels of injurious metals in the fish's blood and tissue. An antimicrobial additive would aid the fish by reducing the risk of infection from the hook or other injury to the fish. A preservative additive would aid the fish by ensuring that one or more of the components of the composition do not degrade before use. A color additive in the form of non-toxic dye, pigment, or substance that imparts color would aid the angler to temporarily mark the areas of fish to which the composition was applied.

Oxygenated Substrate Examples. The composition could include an oxygenated substrate, which could comprise, for example and without limitation, one of more of the following: oxygen, perfluorocarbon, and metal hydroxide. Where the oxygenated substrate is oxygen, the composition may be stored under pressure (so as to dissolve the oxygen under pressure in water) and then delivered to the fish by use of a spray mechanism. In this example, dosage would be 3 to 4 sprays from a typical atomizer sprayer. The benefits of this exemplary option would be that the spray can be applied with one hand and can cover the fish's body easily. Inventors estimate that a spray bottle with a 1 oz capacity could deliver a dosage of 0.5 mL for approximately 59 fish. Delivery of oxygen as the oxygenated substrate could also be accomplished via a dropper (similar to the droppers used with hemp oil products). In this exemplary option, the dosage would likely be approximately 1 mL per fish applied to the mouth and gills. Application could also be made directly into the throat of the fish. A typical dropper with a volume of 1 oz would have enough of the composition for 29 fish. Perfluorocarbon could also be used for the oxygenated substrate. Metal hydroxide could also be used for the oxygenated substrate.

Trophic Hormone Examples. The composition could include a trophic hormone, which could comprise, for example and without limitation, a prolactin to stimulate native mucus secretion. Prolactin can be used as a purified substance or as fresh, ground, minced, dried, powdered or solvent-extracted matter from animal tissues, organs, or engineered animal, plant, algae, insect, fungal, or bacterial cells and cultivation media that produce or accumulate prolactin.

Stress-Relieving Additives. The composition could include one or more stress-relieving additive, which may comprise, for example and without limitation, one or more of the following: botanical extracts such as licorice root or garlic clove, botanical essential oils such as eucalyptus, mint, or basil, among others.

Chelating Agent Examples. The composition could include a chelating agent, which maybe, for example and without limitation, ethylenediaminetetraacetic acid.

Preserving Agent Examples. The composition could also include a preserving agent, which may be, for example and without limitation, potassium sorbate.

Color Additive Examples. The composition could also include a color additive in the form of non-toxic dye, pigment, or substance that imparts color, which maybe, for example and without limitation, include carotenoids, anthocyanins, betanins.

Additional Additives Example. Further additives may include, without limitation: alginate to promote the fish's immune system, ergosan, green tea, ginger, polypore mushroom, *Sophora flavescens*, probiotics, immuniostimulants, plant products, oral vaccines for fish, *Euphorbia hirta*, jungle geranium, *Ixora coccinea*, kudzu vine, loquat, lupin, mango, neem, night jasmine, peppermint, stinging nettle, turmeric, or other natural compounds.

Composition Administration Examples. The present invention is illustrated in further detail with reference to the following non-limiting example composition administrations:

The composition may be administered to the fish in a number of manners. For example, without limitation, the composition may be administered orally, topically, internally, anally, or otherwise to any other localized tissue associated with oxygen exchange in a fish (e.g., gills, labyrinth, esophagus, stomach, intestine, swim bladder, oral cavity, and skin) that has been caught and potentially removed temporarily from the water. As discussed above, the oral or topical administration may be accomplished using a spray mechanism or mister or a medicine dropper. Depending upon the particular constituents included in the composition, the container holding the composition may preferably be substantially air-tight and may be tinted or otherwise have a coating to minimize the effect of sunlight on the composition while it is contained within the container. The composition may further be tinted, using a food colorant, or otherwise nontransparent. The tinting or non-transparent feature of the composition will aid in the administration of the composition by the angler to the fish.

The composition may use a carrier to deliver the composition to the fish in a number of manners, for example and without limitation, by a pill, pellet, solution, gel, paste, cream, spray, enema, direct delivery to the swim bladder with a hypodermic or barotrauma device, wash, emersion, as part of artificial bait, as part of a floatant, or as part of a lure. In particular, the composition may be mixed with a cured polymer and formed into the shape of the artificial bait. The composition may also be used with a barotrauma device during hypodermic fizzing or venting event that may be performed to relieve barotrauma effects in fish.

In a preferred embodiment, the composition was delivered to the fish via a bag-on-valve system, wherein the composition is held in a nonreactive bag inside of a pressurized aerosol can equipped with a one way application value. A bag-on-valve delivery system is preferrable because the aerosol necessary to pressurize the delivery system remains separated from the composition that is administered to the fish. Aerosol is a preferred propellant because it is nonflammable and can withstand exposure to heat and cold. Additionally, a bag-on-valve is beneficial because the composition is contained in a nonreactive bag, the likelihood of unwanted oxidation is reduced, ensuring the purity and consistency of the composition. This ensures that the composition within the bag remains viable longer.

Even when the composition is incorporated into artificial bait, it may also be independently dispersed onto the localized tissue associated with oxygen exchange in fish when the first is caught.

Alternative Embodiments. Alternatively, in some embodiments, internal application of the composition may be accomplished without a hydrocolloid. Internal applications routes include an oral gavage, enema, hypodermal barotrauma fizzing, pill, pellet, or capsule. These applications may be completed without a hydrocolloid as a part of the composition as temporary adhesion is not necessary. Experimental Evidence of Benefits to be Determined in Zebrafish Zebrafish are commonly used as a vertebrate fish model organism for various traits including swimming performance, metabolism, disease, and phenotypic characterization. Central to many of these studies is the ability to easily and reliably assay zebrafish swimming performance, exhaustion, exercise, and recovery which are essential for evaluating fish health, wellbeing, and metabolic performance.

This study utilizes a well-recognized vessel plunger model system to determine fish exhaustion during maximal swim performance trials (Usui T, Noble D W A, O'Dea R E, Fangmeier M L, Lagisz M, Hesselson D, Nakagawa S. The French press: a repeatable and high-throughput approach to exercising zebrafish (*Danio rerio*). PeerJ. 2018 6: e4292). In brief, zebrafish is placed in the top compartment above plunger and evaluated for its ability to swim against circular water currents created by a rotating magnetic stir bar positioned below the plunger. The individual maximum swimming speed is determined by increasing the stirrer speed at 10 rpm steps every 5 seconds until maximum swimming speed and exhaustion are achieved, defined as the speed at which zebrafish lost ability to maintain position in the water column (pre-exhaustion value). Next, the fish is brought to the water surface with the aid of a plunger and the composition is administered to the fish using one of the possible methods of administration. The fish is lowered back into the top compartment, and the individual maximum swimming speed is determined again (post-exhaustion value).

This experimental setup allows one to determine the highest tolerated continuous swimming speed associated with control, exhaustion and recovery conditions that models catching, fighting, landing, treating, and releasing fish.

Applicant anticipated use of the disclosed composition to test which embodiments provide the greatest reduction in mortality following a catch-and-release situation. Such a test has now been completed, and Applicant's findings are discussed in Experiment 1, below.

Experiment 1—Zebrafish Swim Exhaustion Test

Applicant investigated exhaustion rates for Zebrafish, *Danio rerio*, which had been swam to exhaustion, then administered one of 13 compounds (including a control), then swam to exhaustion 20 minutes later, and again 24 hours later. The experimental methodology was substantially similar to the methods discussed in Usui, et al. (2018).

Results show fish swim failures across 12 treatments and 1 control, and at two time intervals: prior to exhaustion ("Initial swim strength 0 min"), and 20 minutes after application of the treatment, post exhaustion ("Immediate recovery, 20 minutes later"). Initial swim strength was measured prior to exhaustion of the fish and subsequent administration of the selected treatment and therefore serves as a baseline. While other treatments did not yield statistically significant results, Applicant believes further testing, increased sample sizes, and compounding positive effects of multiple ingredients may increase fish survivability.

After the initial swim strength test, the fish swam to exhaustion (as defined in Usui, et al. (2018)) and then the selected treatment (including control) was administered, and 20 minutes later the swim exhaustion test was repeated. As anticipated by the Applicant, even post-treatment the fish became exhausted at a lower rpm, but there were significant differences in when each treatment group began to tire.

TABLE 1

| | Treatments | | | | | | | | | | | | | | |
|---|---|---|---|---|---|---|---|---|---|---|---|---|---|---|---|
| | Initial swim strength 0 min | | | | | | | | Immediate recovery 20 min later | | | | | | |
| Water control | 560 | 660 | 670 | 570 | 650 | 720 | 640 | 690 | 420 | 510 | 450 | 350 | 460 | 370 | 390 | 360 |
| Air bubbled water | 690 | 570 | 620 | 670 | 510 | 540 | 720 | 710 | 490 | 420 | 450 | 470 | 450 | 440 | 450 | 520 |
| Formula H2O2PVP | 550 | 700 | 590 | 550 | 690 | 660 | 720 | 660 | 570 | 450 | 580 | 450 | 570 | 470 | 580 | 600 |
| Sodium percarbonate | 600 | 560 | 560 | 710 | 660 | 600 | 680 | 690 | 540 | 540 | 500 | 590 | 530 | 430 | 520 | 460 |
| Polyvinyl-pyrrolidone (PVP) | 580 | 550 | 710 | 590 | 570 | 620 | 680 | 660 | 410 | 460 | 420 | 490 | 480 | 390 | 480 | 400 |
| Hyaluronic acid | 600 | 610 | 580 | 580 | 590 | 670 | 540 | 540 | 400 | 400 | 490 | 490 | 480 | 460 | 490 | 420 |
| Essential oil, mint | 530 | 620 | 550 | 580 | 630 | 630 | 640 | 600 | 440 | 500 | 490 | 410 | 430 | 500 | 450 | 500 |
| Garlic clove, extract | 500 | 500 | 670 | 560 | 570 | 550 | 620 | 700 | 480 | 500 | 530 | 500 | 420 | 420 | 420 | 430 |
| Pyruvate | 590 | 720 | 520 | 740 | 530 | 550 | 610 | 610 | 410 | 420 | 430 | 450 | 510 | 520 | 420 | 450 |
| Leucine | 650 | 650 | 610 | 550 | 690 | 640 | 700 | 550 | 460 | 400 | 470 | 510 | 490 | 390 | 400 | 470 |
| Arginine | 520 | 570 | 570 | 570 | 700 | 550 | 510 | 700 | 280 | 520 | 520 | 510 | 550 | 450 | 580 | 460 |
| Salt | 620 | 580 | 590 | 690 | 580 | 680 | 670 | 660 | 480 | 410 | 490 | 510 | 510 | 490 | 480 | 400 |
| EDTA | 590 | 500 | 600 | 500 | 640 | 640 | 500 | 610 | 460 | 460 | 430 | 410 | 420 | 520 | 460 | 410 |
| Potassium sorbate | 510 | 630 | 630 | 550 | 580 | 550 | 570 | 670 | 410 | 380 | 420 | 440 | 460 | 460 | 390 | 500 |

Applicant administered the following treatments: water, air-bubbled water, formula polyvinylpyrrolidone-hydrogen peroxide complex (PVP-$H_2O_2$) sodium percarbonate ($Na_2H_3CO_6$), hyaluronic acid, essential oil (mint extract), garlic clove extract, pyruvate, leucine, arginine, salt, EDTA, and potassium sorbate. Each treatment was administered to eight Zebrafish (n=104 total fish). Table 1 reports individual fish swim-exhaustion/fail results for each treatment. Results in Table 1 are water vortex revolutions per minute when the subject fish failed to maintain swimming in place.

Table 1 shows results for individual fish. Each treatment group contained eight fish, which were each tested at three times: prior to exhaustion, and 20 minutes post exhaustion/treatment. The averages of these results, and any statistical significance of the treatments are shown in Table 2.

Table 2 reports the average swim exhaustion results, standard deviations, change from the control treatment (as a percentage of the control treatment), and whether any treatment had a statistically significant impact on immediate recovery.

TABLE 2

| | Statistical analysis | | | | | | | |
|---|---|---|---|---|---|---|---|---|
| | Initial swim strength 0 min | | | | Immediate recovery 20 min later | | | |
| | Average | SD | % Control | Significance | Average | SD | % Control | Significance |
| Water control | 645 | 55 | n/a | n/a | 414 | 56 | 0 | |
| Air bubbled water | 629 | 81 | n/a | n/a | 461 | 31 | 11 | |
| Formula H2O2PVP | 640 | 68 | n/a | n/a | 534 | 65 | 29 | * |
| Sodium percarbonate | 633 | 60 | n/a | n/a | 514 | 50 | 24 | * |
| Polyvinylpyrrolidone (PVP) | 620 | 58 | n/a | n/a | 441 | 41 | 7 | |

TABLE 2-continued

| | Statistical analysis | | | | | | | |
| | Initial swim strength 0 min | | | | Immediate recovery 20 min later | | | |
| | Average | SD | % Control | Significance | Average | SD | % Control | Significance |
|---|---|---|---|---|---|---|---|---|
| Hyaluronic acid | 589 | 42 | n/a | n/a | 454 | 41 | 10 | |
| Essential oil, peppermint | 598 | 41 | n/a | n/a | 465 | 37 | 12 | |
| Garlic clove, extract | 584 | 74 | n/a | n/a | 463 | 45 | 12 | |
| Pyruvate | 609 | 82 | n/a | n/a | 451 | 42 | 9 | |
| Leucine | 630 | 57 | n/a | n/a | 455 | 41 | 10 | |
| Arginine | 586 | 74 | n/a | n/a | 484 | 93 | 17 | * |
| Salt | 634 | 47 | n/a | n/a | 471 | 43 | 14 | |
| EDTA | 573 | 63 | n/a | n/a | 446 | 37 | 8 | |
| Potassium sorbate | 586 | 53 | n/a | n/a | 433 | 40 | 5 | |

Table 2 shows the formula polyvinylpyrrolidone-hydrogen peroxide complex ($H_2O_2PVP$), sodium percarbonate ($Na_2H_3CO_6$), and the amino acid Arginine each had a significant effect on a fish's immediate recovery, allowing fish to swim through water moving 29%, 24%, and 17% more (respectively) than fish that were only treated with a control. This suggests that these treatments would aid fish recovery following a stressful event, such as a catch-and-release event, and that these fish would tire less quickly, and therefore likely have a stronger chance to survive predation and have an overall higher chance of survival in the wild.

Although all test treatments had a higher average swim failure number (and therefore, appeared to be stronger healthier fish, capable of swimming against a higher rpm), none of the other treatments had a statistically significant effect on fish swim fail rates.

In Experiment 1, fish swim exhaustion rates served as a proxy for fish mortality. The Applicant's goal is to increase fish survival rates in the wild following a catch-and-release event. The experimental design tested fish swimming exhaustion with the goal of avoiding unnecessarily torturing the fish while still obtaining relevant data. In particular, Applicant believes that the fish exhaustion test and recovery rates are approximate, albeit more benign, proxy of fish mortality in the wild following a catch-and-release event. Among other potential distinctions, the experiment, unlike a catch-and-release event, did not subject the test fish to prolonged oxygen deprivation or the additional potential harm and trauma caused by hook removal. The more a fish is exhausted from a catch-and-release event, the more likely that fish is to die from predation, stress, or other environmental hazards.

Further, the data from Experiment 1 provide direct evidence that the treatments disclosed by Applicant will aid a fish to recover from exhaustion in an environment where they are increasingly likely to be caught and released in potentially relatively short periods of time, even within 20 minutes. This will improve fish survival rates. As the popularity of sport fishing increases and the harmful impacts of climate change persist, short-term stressors on fish will also increase. Drought, sever weather events, loss of habitat and other climate-driven factors may reduce the number of locations fish are able to grow, reproduce and thrive. Likewise, as the demand for sport fishing increases among anglers and conservationists, it is conceivable that a fish may be caught and released multiple times in a single day, thereby compounding the harmful effects related to a catch-and-release sport fishing, and underscoring the importance of short-term recovery treatments to the fish.

What is claimed is:

1. A method of increasing the likelihood that a fish caught by an angler in the wild survives its release back into the wild, the method comprising:
    after catching the fish, applying a composition to the fish, wherein the composition includes an energy substrate and a hydrocolloid; and
    releasing the fish back into the wild.

2. The method of claim 1 wherein the composition further includes an application-safe buffer.

3. The method of claim 2 wherein the application-safe buffer is designed to balance the pH of the fish.

4. The method according to claim 1 wherein applying the composition is generally directed to a localized tissue associated with oxygen exchange in fish.

5. The method according to claim 4 wherein the localized tissue associated with oxygen exchange in fish is selected from the group consisting of gills, labyrinth, esophagus, stomach, intestine, swim bladder, oral cavity, skin, and combinations thereof.

6. The method according to claim 1 wherein applying the composition is performed by spraying a therapeutic amount of the composition from a spray bottle.

7. The method according to claim 1 wherein applying the composition is performed using a medicine dropper to drop a therapeutic amount of the composition from a container into the mouth of the fish.

8. The method according to claim 1 wherein the composition further includes a color additive that allows temporary visualization of the area to which the composition was applied.

9. The method according to claim 1 wherein applying the composition is performed in combination with fizzing or venting performed with a hypodermic device to relieve barotrauma effects in fish.

10. A method of increasing the likelihood that a fish caught by an angler in the wild survives its release back into the wild, the method comprising:
    after catching the fish, applying a composition to the fish, wherein the composition includes an energy substrate and a hydrocolloid;
    wherein the composition is mixed with a cured polymer in the shape of a fishing lure and is dispersed onto the localized tissue associated with oxygen exchange in fish when fish is caught; and
    releasing the fish back into the wild.

11. A method of increasing the likelihood that a fish caught by an angler in the wild survives its release back into the wild, the method comprising:

after catching the fish, applying a composition to the fish,
    wherein the composition includes an energy substrate
    and a hydrocolloid;
wherein the composition is mixed in a combination with
    wax and a carrier and is used as a floatant that is
    dispersed onto the localized tissue associated with
    oxygen exchange in fish when fish is caught; and
releasing the fish back into the wild.

5

\*  \*  \*  \*  \*